US006887691B2

(12) United States Patent
Livshits et al.

(10) Patent No.: US 6,887,691 B2
(45) Date of Patent: May 3, 2005

(54) **DNA CODING FOR PROTEIN WHICH CONFERS ON BACTERIUM *ESCHERICHIA COLI* RESISTANCE TO L-HOMOSERINE, AND METHOD FOR PRODUCING L-AMINO ACIDS**

(75) Inventors: Vitaly Arkadievich Livshits, Moscow (RU); Natalya Pavlovna Zakataeva, Moscow (RU); Vladimir Venyamiovich Aleoshin, Moscow (RU); Alla Valentinovna Balareova, Moscow (RU); Irina Lvovna Tokhmakova, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 20 days.

(21) Appl. No.: 09/847,392

(22) Filed: May 3, 2001

(65) Prior Publication Data

US 2002/0102670 A1 Aug. 1, 2002

Related U.S. Application Data

(63) Continuation of application No. 09/396,357, filed on Sep. 15, 1999, now Pat. No. 6,303,348.

(30) Foreign Application Priority Data

Oct. 13, 1998 (RU) .......................................... 98118425

(51) Int. Cl.⁷ .......................... C12P 13/04; C12P 13/08; C12N 1/20
(52) U.S. Cl. ........................ 435/106; 435/41; 435/69.1; 435/115; 435/116; 435/252.3; 435/320.1; 536/23.2
(58) Field of Search .............................. 435/6, 4, 8–28, 435/41, 69.1, 94–99, 106–116, 183 T, 252.3, 320.1; 536/23.2, 23.7

(56) References Cited

U.S. PATENT DOCUMENTS

| 4,278,765 | A | 7/1981 | Debabov et al. |
| 5,017,483 | A | 5/1991 | Furukawa et al. |
| 5,175,107 | A | 12/1992 | Debabov et al. |
| 5,534,421 | A | 7/1996 | Livshits et al. |
| 5,538,873 | A | 7/1996 | Debabov et al. |
| 5,631,157 | A | 5/1997 | Debabov et al. |
| 5,658,766 | A | 8/1997 | Livshits et al. |
| 5,705,371 | A | 1/1998 | Debabov et al. |
| 5,976,843 | A | 11/1999 | Debabov et al. |
| 6,132,999 | A | 10/2000 | Debabov et al. |
| 6,165,756 | A | 12/2000 | Debabov et al. |
| 6,297,031 | B1 | 10/2001 | Debabov et al. |
| 6,303,348 | B1 | 10/2001 | Livshits et al. |

FOREIGN PATENT DOCUMENTS

| EP | 1 013 765 | 6/2000 |
| WO | 97 23597 | 7/1997 |

OTHER PUBLICATIONS

N. P. Zakataeva, et al., 17th International Congress of Biochemistry and Molecular Biology, "Characterization of a Pleiotropic Mutation That Confers Upon *Escherichia coli* Cells Resistance to High Concentrations of Homoserine and Threonine", Aug. 24–29, 1997.

O.B. Astaurova, et al., Applied Biochemistry and Microbiology, vol. 21, No. 5, pps 485–490, "Amination in Strains of *Escherichia coli* Which Effectively Synthesize Threonine," Mar. 1986.

O.L. Lomovskaya, et al., Journal of Bacteriology, vol. 176, No. 13, pps. 3928–3935, "Characterization of the $\sigma^{38}$–Dependent Expression of a Core *Escherichia coli* Starvation Gene, pexB," Jul. 1994.

O.B. Astaurova, et al., Applied Biochemistry and Microbiology, vol. 27, No. 5, pp. 556–561, "Comparative Study of Amino–Acid–Producing *E. coli* Strains", Mar., 1992.

Daniels et al. Analysis of *E. coli* genome: DNA sequence of the region from 84.5–86–5 minutes. Science, 1992, vol. 257:771–778.

Daniels et al.: "Homoserine/homoserinelactone efflux protein" retrieved from EBI, accession No. RHTB_ECOLI, Database accession No. P27847 XP002202582 *the whole document* –&.

Jan. 29, 1997 Blattner et al.: "*Escherichia coli* K12MG1655 section 348 of 400 of the complete genome" retrieved from EBI, accession No. ECAE458 Database accession No. AE000458 XP002202583 *the whole document* &.

Zakataeva et al.: "The novel transmembrane *Escherichia coli* proteins involved in the amino acid efflux" FEBS Letters, vol. 452, Jun. 11, 1999, pp. 228–232.

Zakataeva et al.: "Characterization of a pleiotropic mutation that confers upon *Escherichia coli* cells resistance to high concentrations of homoserine and threonine" FASEB Journal, Fed. of American Soc. for Experimental Biology, Betheda, MD, US , vol. 11, No. 9, Jul. 31, 1997, p. a935.

Aleshin V. V. et al: "A new family of amino–acid–efflux proteins" TIBS Trends in Biochemical Sciences, Elsevier Publication, Cambridge, En, vol. 24, No. 4, Apr. 1, 1999 pp. 133–135.

*Primary Examiner*—Manjunath N. Rao
(74) *Attorney, Agent, or Firm*—Shelly Guest Cermak (57) ABSTRACT

A bacterium which has an ability to produce an amino acid and in which a novel gene (rhtB) coding for a protein having an activity of making a bacterium having the protein L-homoserine-resistant is enhanced, is cultivated in a culture medium to produce and accumulate the amino acid in the medium, and the amino acid is recovered from the medium.

5 Claims, 2 Drawing Sheets

FIG. 1

```
Met Thr Leu Glu Trp Trp Phe Ala Tyr Leu Leu Thr Ser Ile Ile Leu
 1               5                   10                  15
Thr Leu Ser Pro Gly Ser Gly Ala Ile Asn Thr Met Thr Thr Ser Leu
            20                  25                  30
Asn His Gly Tyr Pro Ala Gly Gly Val Tyr Cys Trp Ala Ser Asp Arg
            35              40                  45
Thr Gly Asp Ser Tyr Cys Ala Gly Trp Arg Gly Val Gly Thr Leu Phe
        50              55                  60
Ser Arg Ser Val Ile Ala Phe Glu Val Leu Lys Trp Ala Gly Ala Ala
 65                  70              75                      80
Tyr Leu Ile Trp Leu Gly Ile Gln Gln Trp Arg Ala Ala Gly Ala Ile
                85                  90                      95
Asp Leu Lys Ser Leu Ala Ser Thr Gln Ser Arg Arg His Leu Phe Gln
            100             105                 110
Arg Ala Val Phe Val Asn Leu Thr Asn Pro Lys Ser Ile Val Phe Leu
            115             120                 125
Ala Ala Leu Phe Pro Gln Phe Ile Met Pro Gln Gln Pro Gln Leu Met
        130             135                 140
Gln Tyr Ile Val Leu Gly Val Thr Thr Ile Val Val Asp Ile Ile Val
145                 150                 155                 160
Met Ile Gly Tyr Ala Thr Leu Ala Gln Arg Ile Ala Leu Trp Ile Lys
                165                 170                 175
Gly Pro Lys Gln Met Lys Ala Leu Asn Lys Ile Phe Gly Ser Leu Phe
            180             185                 190
Met Leu Val Gly Ala Leu Leu Ala Ser Ala Arg His Ala
            195             200             205
(SEQ ID NO: 2)
```

DNA CODING FOR PROTEIN WHICH CONFERS ON BACTERIUM *ESCHERICHIA COLI* RESISTANCE TO L-HOMOSERINE, AND METHOD FOR PRODUCING L-AMINO ACIDS

This application is a continuation of application Ser. No. 09/396,357, filed on Sep. 15, 1999, now U.S. Pat. No. 6,303,348.

TECHNICAL FIELD

The present invention relates to a method for producing an amino acid, especially for a method for producing L-homoserine, L-alanine, L-isoleucine, L-valine, or L-threonine using a bacterium belonging to the genus Escherichia.

BACKGROUND ART

The present inventors obtained, with respect to *E. coli* K-12, a mutant having mutation, thrR, (herein referred to as rhtA23) that is concerned in high concentrations of threonine (>40 mg/ml) or homoserine (>5 mg/ml) in a minimal medium (Astaurova, O. B. et al., Appl. Bioch. and Microbiol., 21, 611–616 (1985)). On the basis of rhtA23 mutation an improved threonine-producing strain (SU patent No. 974817), homoserine- and glutamic acid-producing strains (Astaurova et al., Appl. Boch. And Microbiol., 27, 556–561 (1991)) were obtained.

Furthermore, the present inventors has revealed that the rhtA gene exists at 18 min on *E. coli* chromosome and that the rhtA gene is identical to ORF1 between pexB and ompX genes. The unit expressing a protein encoded by the ORF1 has been designated as rhtA (rht: resistance to homoserine and threonine) gene. The rhtA gene includes a 5'-noncoding region including SD sequence, ORF1 and a terminator. Also, the present inventors have found that a wild type rhtA gene participates in resistance to threonine and homoserine if cloned in a multicopy state and that enhancement of expression of the rhtA gene improves amino acid productivity of a bacterium belonging to the genus *Escherichia* having an ability to produce L-lysine, L-valine or L-threonine (ABSTRACTS of 17th International Congress of Biochemistry and Molecular Biology in conjugation with 1997 Annual Meeting of the American Society for Biochemistry and Molecular Biology, San Francisco, Calif. Aug. 24–29, 1997, abstract No. 457).

It is found that at least two different genes which impart homoserine resistance in a multicopy state exist in *E. coli* during cloning of the rhtA gene. One of the genes is the rhtA gene, however the other gene has not been elucidated.

DISCLOSURE OF THE INVENTION

An object of the present invention is to provide a novel gene participating in resistance to homoserine, and a method for producing an amino acid, especially, L-homoserine, L-alanine, L-isoleucine, L-valine and L-threonine with a high yield.

The inventors have found that a region at 86 min on *E. coli* chromosome, when cloned by a multicopy vector, impart resistance to L-homoserine to cells of *E. coli*, and that when the region is amplified, the amino acid productivity of *E. coli* can be improved like the rhtA gene. On the basis of these findings, the present invention have completed.

Thus, the present invention provides:
(1) a DNA coding for a protein as defined in the following (A) or (B):

(A) a protein which comprises an amino acid sequence shown in SEQ ID NO: 2 in Sequence Listing; or
(B) a protein which comprises an amino acid sequence including deletion, substitution, insertion or addition of one or several amino acids in the amino acid sequence shown in SEQ ID NO: 2 in Sequence Listing, and which has an activity of making a bacterium having the protein L-homoserine-resistant,
(2) the DNA according to (1), which is a DNA as defined in the following (a) or (b):
(a) a DNA which comprises a nucleotide sequence corresponding to the nucleotide numbers of 557 to 1171 of a nucleotide sequence shown in SEQ ID NO: 1 in Sequence Listing; or
(b) a DNA which hybridizes with the nucleotide sequence corresponding to the nucleotide numbers of 557 to 1171 of the nucleotide sequence shown in SEQ ID NO: 1 in Sequence Listing under stringent conditions, and which codes for the protein having the activity of making the bacterium having the protein L-homoserine-resistant,
(3) a bacterium belonging to the genus *Escherichia*, wherein L-homoserine resistance of the bacterium is enhanced by amplifying a copy number of the DNA of (1) in a cell of the bacterium,
(4) the bacterium of (3), wherein the DNA of (1) is carried on a multicopy vector in the cell of the bacterium,
(5) the bacterium of (3), wherein the DNA of (1) is carried on a transposon in the cell of the bacterium,
(6) a method for producing an amino acid, comprising the steps of cultivating the bacterium of any of (3) to (5), which has an ability to produce the amino acid, in a culture medium to produce and accumulate the amino acid in the medium, and recovering the amino acid from the medium, and
(7) the method of (6), wherein the amino acid is at least one selected from the group consisting of L-homoserine, L-alanine, L-isoleucine, L-valine and L-threonine.

The DNA of the present invention may be referred to as "rhtB gene", a protein coded by the rhtB gene may be referred to as "RhtB protein", an activity of the RhtB protein which participates in resistance to L-homoserine of a bacterium (i.e. an activity of making a bacterium having the RhtB protein L-homoserine-resistant) may be referred to "Rh activity", and a structural gene encoding the RhtB protein in the rhtB gene may be referred to as "rhtB structural gene". The term "enhancing the Rh activity" means imparting resistance to homoserine to a bacterium or enhancing the resistance by means of increasing the number of molecules of the RhtB protein, increasing a specific activity of the RhtB protein, or desensitizing negative regulation against the expression or the activity of the RhtB protein or the like. The terms "DNA coding for a protein" mean a DNA of which one of strands codes for the protein when the DNA is double-stranded. The L-homoserine resistance means a property that a bacterium grows on a minimal medium containing L-homoserine at a concentration at which a wild type strain thereof can not grow, usually at 10 mg/ml. The ability to produce an amino acid means a property that a bacterium produces an accumulates the amino acid in a medium in a larger amount than a wild type strain thereof.

According to the present invention, resistance to homoserine of a high concentration can be imparted to a bacterium belonging to the genus *Escherichia*. A bacterium belonging to the genus *Escherichia*, which has increased resistance homoserine and an ability to produce an amino acid, accumulates an amino acid, especially, L-homoserine, L-alanine, L-isoleucine, L-valine or L-threonine in a medium with a high yield.

The present invention will be explained in detail below.
<1> DNA of the Present Invention The DNA of the present invention may code for a protein having the Rh activity and having an amino acid sequence shown in SEQ ID NO: 2 in Sequence Listing. Specifically, the DNA of the present invention may be exemplified by a DNA comprising a nucleotide sequence of the nucleotide numbers 557 to 1171 of a nucleotide sequence shown in SEQ ID NO: 1 in Sequence Listing.

The DNA of the present invention includes a DNA fragment encoding the RhtB protein conferring bacterium *Escherichia coli* resistance to homoserine, which includes the regulatory elements of the rhtB gene and the structural part of rhtB gene, having the nucleotide sequence shown in SEQ ID NO: 1.

The nucleotide sequence shown in SEQ ID NO: 1 corresponds to a part of sequence complement to the sequence of GenBank accession number M87049. SEQ ID NO: 1 includes f138 (nucleotide numbers 61959-61543 of GenBank accession number M87049) which is a known but function-unknown ORF (open reading frame) present at 86 min on *E. coli* chromosome, and 5'-flanking and 3'-flanking regions thereof. The f138, which had only 160 nucleotides in the 5'-flanking region, could not impart the resistance to homoserine. No termination codon is present between the 62160 and 61959 of M87049 (upstream the ORF f138). Hence, the coding region is 201 bp longer. Thus the RhtB protein and the rhtB gene coding for the protein are novel.

The rhtB gene may be obtained, for example, by infecting Mucts lysogenic strain of *E. coli* using a lysate of a lysogenic strain of *E. coli* such as K12 or W3110 according to the method in which mini-Mu d5005 phagemid is used (Groisman, E. A., et al., J. Bacteriol., 168, 357–364 (1986)), and isolating plasmid DNAs from colonies growing on a minimal medium containing kanamycin (40 μg/ml) and L-homoserine (10 mg/ml). As illustrated in the Example described below, the rhtB gene was mapped at 86 min on the chromosome of *E. coli*. Therefore, the DNA fragment including the rhtB gene may be obtained from the chromosome of *E. coli* by colony hybridization or PCR (polymerase chain reaction, refer to White, T. J. et al, Trends Genet. 5, 185(1989)) using oligonucleotide(s) which has a sequence corresponding to the region near the portion of 86 min on the chromosome of *E. coli*. Alternatively, the oligonucleotide may be designed according to the nucleotide sequence shown in SEQ ID NO: 1. By using oligonucleotides having nucleotide sequences corresponding to a upstream region from the nucleotide number 557 and a downstream region from the nucleotide number 1171 in SEQ ID NO: 1 as the primers for PCR, the entire coding region can be amplified.

Synthesis of the oligonucleotides can be performed by an ordinary method such as a phosphoamidite method (see Tetrahedron Letters, 22, 1859 (1981)) by using a commercially available DNA synthesizer (for example, DNA Synthesizer Model 380B produced by Applied Biosystems). Further, the PCR can be performed by using a commercially available PCR apparatus (for example, DNA Thermal Cycler Model PJ2000 produced by Takara Shuzo Co., Ltd.), using Taq DNA polymerase (supplied by Takara Shuzo Co., Ltd.) in accordance with a method designated by the supplier.

The DNA coding for the RhtB protein of the present invention may code for RhtB protein including deletion, substitution, insertion, or addition of one or several amino acids at one or a plurality of positions, provided that the Rh activity of RhtB protein encoded thereby is not deteriorated.

The DNA, which codes for the substantially same protein as the RhtB protein as described above, may be obtained, for example, by modifying the nucleotide sequence, for example, by means of the site-directed mutagenesis method so that one or more amino acid residues at a specified site involve deletion, substitution, insertion or addition. DNA modified as described above may be obtained by the conventionally known mutation treatment. The mutation treatment includes a method for treating a DNA coding for the RhtB protein in vitro, for example, with hydroxylamine, and a method for treating a microorganism, for example, a bacterium belonging to the genus *Escherichia* harboring a DNA coding for the RhtB protein with ultraviolet irradiation or a mutating agent such as N-methyl-N'-nitro-N-nitrosoguanidine (NTG) and nitrous acid usually used for the mutation treatment.

The DNA, which codes for substantially the same protein as the RhtB protein, can be obtained by expressing a DNA subjected to in vitro mutation treatment as described above in multicopy in an appropriate cell, investigating the resistance to homoserine, and selecting the DNA which increases the resistance. Also, it is generally known that an amino acid sequence of a protein and a nucleotide sequence coding for it may be slightly different between species, strains, mutants or variants, and therefore the DNA, which codes for substantially the same protein, can be obtained from L-homoserine resistant species, strains, mutants and variants belonging to the genus *Escherichia*. Specifically, the DNA, which code for substantially the same protein as the RhtB protein, can be obtained by isolating DNA which hybridizes with DNA having, for example, a nucleotide sequence of the nucleotide numbers 557 to 1171 of the nucleotide sequence shown in SEQ ID NO: 1 in Sequence Listing under stringent conditions, and which codes for a protein having the Rh activity, from bacterium belonging to the genus *Escherichia* which is subjected to mutation treatment, or spontaneous mutant or a variant of a bacterium belonging to the genus *Escherichia*. The term "stringent conditions" referred to herein is a condition under which so-called specific hybrid is formed, and non-specific hybrid is not formed. It is difficult to clearly express this condition by using any numerical value. However, for example, the stringent conditions include a condition under which DNAs having high homology, for example, DNAs having homology of not less than 70% with each other are hybridized, and DNAs having homology lower than the above with each other are not hybridized.

<2>Bacterium Belonging to the Genus *Escherichia* of the Present Invention

The bacterium belonging the genus *Escherichia* of the present invention is a bacterium belonging to the genus *Escherichia* of which the Rh activity is enhanced. A bacterium belonging to the genus *Escherichia* is exemplified by *Escherichia coli*. The Rh activity can be enhanced by, for example, amplification of the copy number of the rhtB structural gene in a cell, or transformation of a bacterium belonging to the genus *Escherichia* with a recombinant DNA in which a DNA fragment including the rhtB structural gene encoding the RhtB protein is ligated with a promoter sequence which functions efficiently in a bacterium belonging to the genus *Escherichia*. The Rh activity can be also enhanced by substitution of the promoter sequence of the rhtB gene on a chromosome with a promoter sequence which functions efficiently in a bacterium belonging to the genus *Escherichia*.

The amplification of the copy number of the rhtB structural gene in a cell can be performed by introduction of a multicopy vector which carries the rhtB structural gene into a cell of a bacterium belonging to the genus *Escherichia*. Specifically, the copy number can be increased by introduction of a plasmid, a phage or a transposon (Berg, D. E. and Berg, C. M., Bio/Technol., 1, 417 (1983)) which carries the rhtB structural gene into a cell of a bacterium belonging to the genus *Escherichia*.

The multicopy vector is exemplified by plasmid vectors such as pBR322, pMW118, pUC19 or the like, and phage vectors such as λ1059, λBF101, M13mp9 or the like. The transposon is exemplified by Mu, Tn10, Tn5 or the like.

The introduction of a DNA into a bacterium belonging to the genus *Escherichia* can be performed, for example, by a method of D. M. Morrison (Methods in Enzymology 68, 326 (1979)) or a method in which recipient bacterial cells are treated with calcium chloride to increase permeability of DNA (Mandel, M. and Higa, A., J. Mol. Biol., 53, 159 (1970)) and the like.

If the Rh activity is enhanced in an amino acid-producing bacterium belonging to the genus *Escherichia* as described above, a produced amount of the amino acid can be increased. As the bacterium belonging to the genus *Escherichia* which is to be the Rh activity is enhanced, strains which have abilities to produce desired amino acids are used. Besides, an ability to produce an amino acid may be imparted to a bacterium in which the Rh activity is enhanced. Examples of amino acid-producing bacteria belonging to the genus *Escherichia* are described below.

(1) L-threonine-producing Bacteria

The L-threonine-producing bacteria belonging to the genus *Escherichia* may be exemplified by strain MG442 (Guayatiner et al., Genetika (in Russian), 14, 947–956 (1978)).

(2) L-homoserine-producing Bacteria

The L-homoserine-producing bacteria belonging to the genus *Escherichia* may be exemplified by strain NZ10 (thrB). This strain was derived from the known strain C600 (thrB, leuB) (Appleyard R. K., Genetics, 39, 440–452 (1954)) as Leu$^+$ revertant.

On the basis of the rhtB DNA fragment, new amino acid-producing strains *E. coli* NZ10/pAL4,pRhtB; *E. coli* MG422/pVIC40,pRhtB; and *E. coli* MG442/pRhtB were obtained which are used for the production of amino acids by fermentation.

The new strains have been deposited (according to international deposition based on Budapest Treaty) in the Russian National Collection of Industrial Microorganisms (VKPM) on Oct. 6, 1998. The strain *E. coli* NZ10/pAL4, pRhtB has been deposited as an accession number of VKPM B-7658; the strain *E. coli* MG442/pRhtB has been deposited as an accession number of VKPM B-7659; and the strain *E. coli* MG442/pVIC40,pRhtB has been deposited as an accession number of VKPM B-7660.

The strain *E. coli* NZ10/pAL4,pRhtB (VKPM B-7658) exhibits the following cultural-morphological and biochemical features.

Cytomorphology. Gram-negative weakly-motile rods having rounded ends. Longitudinal size, 1.5 to 2 µm.

Cultural Features:

Beef-extract Agar. After 24-hour growth at 37° C., produces round whitish semitransparent colonies 1.5 to 3 mm in diameter, featuring a smooth surface, regular or slightly wavy edges, the center is slightly raised, homogeneous structure, pastelike consistency, readily emulsifiable.

Luria's Agar. After a 24-hour growth at 37° C., develops whitish semitranslucent colonies 1.5 to 2.5 mm in diameter having a smooth surface, homogeneous structure, pastelike consistency, readily emulsifiable.

Minimal Agar-doped Medium M9. After 40 to 48 hours of growth at 37° C., forms colonies 0.5 to 1.5 mm in diameter, which are colored greyish-white, semitransparent, slightly convex, with a lustrous surface.

Growth in a Beef-extract Broth. After 24-hour growth at 37° C., exhibits strong uniform cloudiness, has a characteristic odor.

Physiological and Biochemical Features:

Grows upon thrust inoculation in a beef-extract agar.
Exhibits good growth throughout the inoculated area.
The microorganism proves to be a facultative anaerobe.
It does not liquefy gelatin.
Features a good growth on milk, accompanied by milk coagulation.
Does not produce indole.
Temperature Conditions. Grows on beef-extract broth at 20–42° C., an optimum temperature lying within 33–37° C.
pH Value of Culture Medium. Grows on liquid media having the pH value from 6 to 8, an optimum value being 7.2.
Carbon Sources. Exhibits good growth on glucose, fructose, lactose, mannose, galactose, xylose, glycerol, and mannitol to produce an acid and gas. Nitrogen sources. Assimilates nitrogen in the form of ammonium, nitric acid salts, as well as from some organic compounds.
Resistant to ampicillin, kanamycin and L-homoserine.
L-Threonine is used as a growth factor.
Content of Plasmids. The cells contain multicopy hybrid plasmid pAL4 ensuring resistance to ampicillin and carrying the gene thrA of the threonine operon, which codes for aspartate kinase-homoserine dehydrogenase I responsible for the increased homoserine biosynthesis. Besides, the cells contain a multicopy hybrid plasmid pRhtB ensuring resistance to kanamycin and carrying the rhtB gene which confers resistance to homoserine (10 mg/l).

The strain *E. coli* MG442/pRhtB (VKPM B-7659) has the same cultural-morphological and biochemical features as the strain NZ10/pAL4,pRhtB except for L-isoleucine is used as a growth factor instead of L-threonine. However, the strain can grow slowly without isoleucine. Besides, the cells of the strain contain only one multicopy hybrid plasmid pRhtB ensuring resistance to kanamycin and carrying the rhtB gene which confers resistance to homoserine (10 mg/l).

The strain *E. coli* MG442/pVIC40,pRhtB (VKPM B-7660) has the same cultural-morphological and biochemical features as the strain NZ10/pAL4,pRhtB except for L-isoleucine is used as a growth factor instead of L-threonine. However, the strain can grow slowly without isoleucine. The cells of the strain contain multicopy hybrid plasmid pVIC40 ensuring resistance to streptomycin and carrying the genes of the threonine operon. Besides, they contain multicopy hybrid plasmid pRhtB ensuring resistance to kanamycin and carrying the rhtB gene which confers resistance to homoserine (10 mg/l).

<3> Method for Producing an Amino Acid

An amino acid can be efficiently produced by cultivating the bacterium in which the Rh activity is enhanced by amplifying a copy number of the rhtB gene as described above, and which has an ability to produce the amino acid, in a culture medium, to produce and accumulate the amino acid in the medium, and recovering the amino acid from the medium. The amino acid is exemplified preferably by L-homoserine, L-alanine, L-isoleucine, L-valine and L-threonine.

In the method of present invention, the cultivation of the bacterium belonging to the genus *Escherichia*, the collection and purification of amino acid from the liquid medium may be performed in a manner similar to those of the conventional method for producing an amino acid by fermentation using a bacterium. A medium used in cultivation may be either a synthetic medium or a natural medium, so long as the medium includes a carbon and a nitrogen source and minerals and, if necessary, nutrients which the bacterium used requires for growth in appropriate amounts. The carbon source may include various carbohydrates such as glucose and sucrose, and various organic acids. Depending on assimilatory ability of the used bacterium, alcohol including ethanol and glycerol may be used. As the nitrogen source, ammonia, various ammonium salts such as ammonium sulfate, other nitrogen compounds such as amines, a natural nitrogen source such as peptone, soybean hydrolyte and digested fermentative microbe are used. As minerals, monopotassium phosphate, magnesium sulfate, sodium chloride, ferrous sulfate, manganese sulfate, calcium carbonate are used.

The cultivation is preferably culture under an aerobic condition such as a shaking culture, and an aeration and stirring culture. The temperature of culture is usually 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 3-day cultivation leads to the accumulation of the target amino acid in the medium.

Recovering the amino acid can be performed by removing solids such as cells from the medium by centrifugation or membrane filtration after cultivation, and then collecting and purifying the target amino acid by ion exchange, concentration and crystalline fraction methods and the like.

EXAMPLES

The present invention will be more concretely explained below with reference to Examples. In the Examples, an amino acid is of L-configuration unless otherwise noted.

Example 1

Obtaining of rhtB DNA Fragment
(1) Cloning of rhtB Gene into Mini-Mu Phagemid

Figure 1:
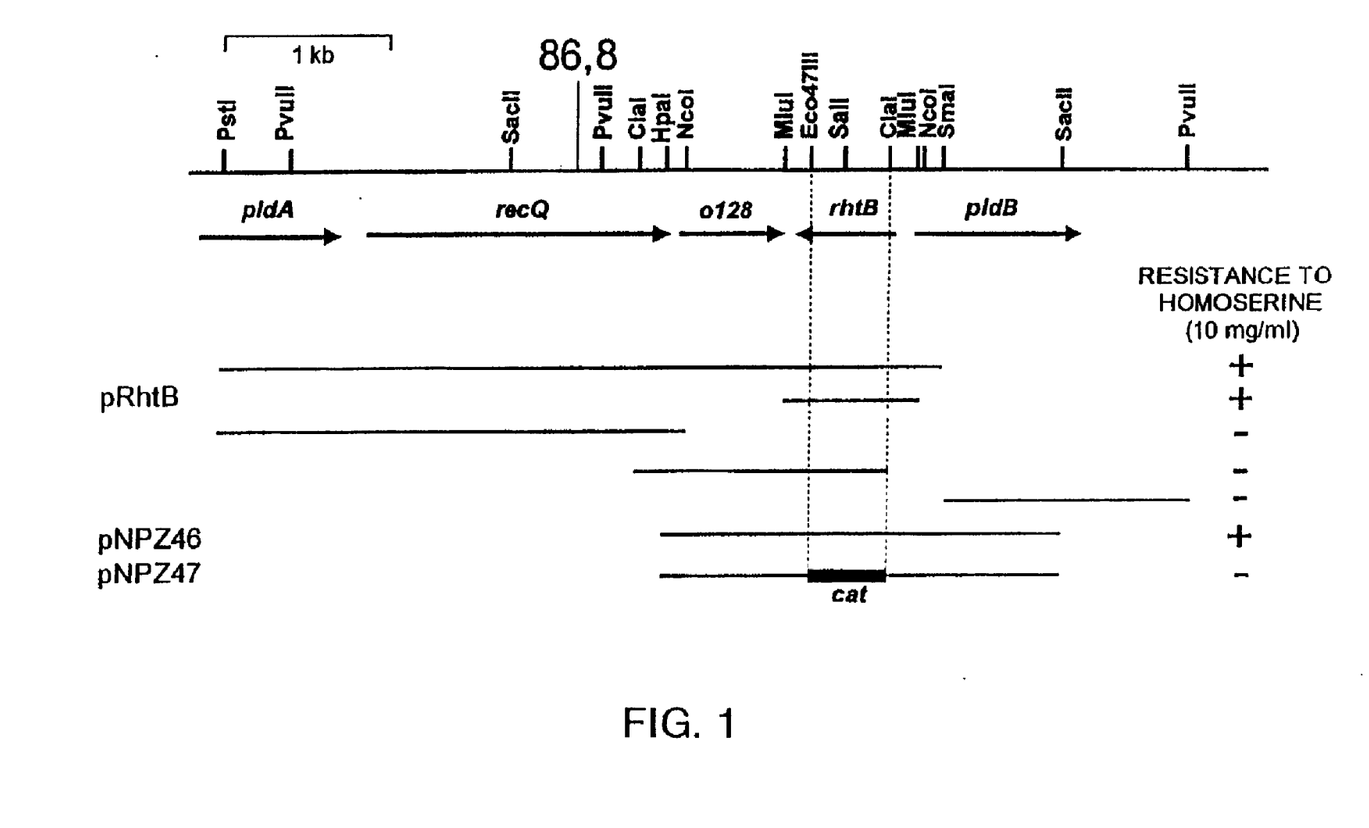
FIG. 1 shows cloning, identification and inactivation of the rhtB gene.
Figure 2:
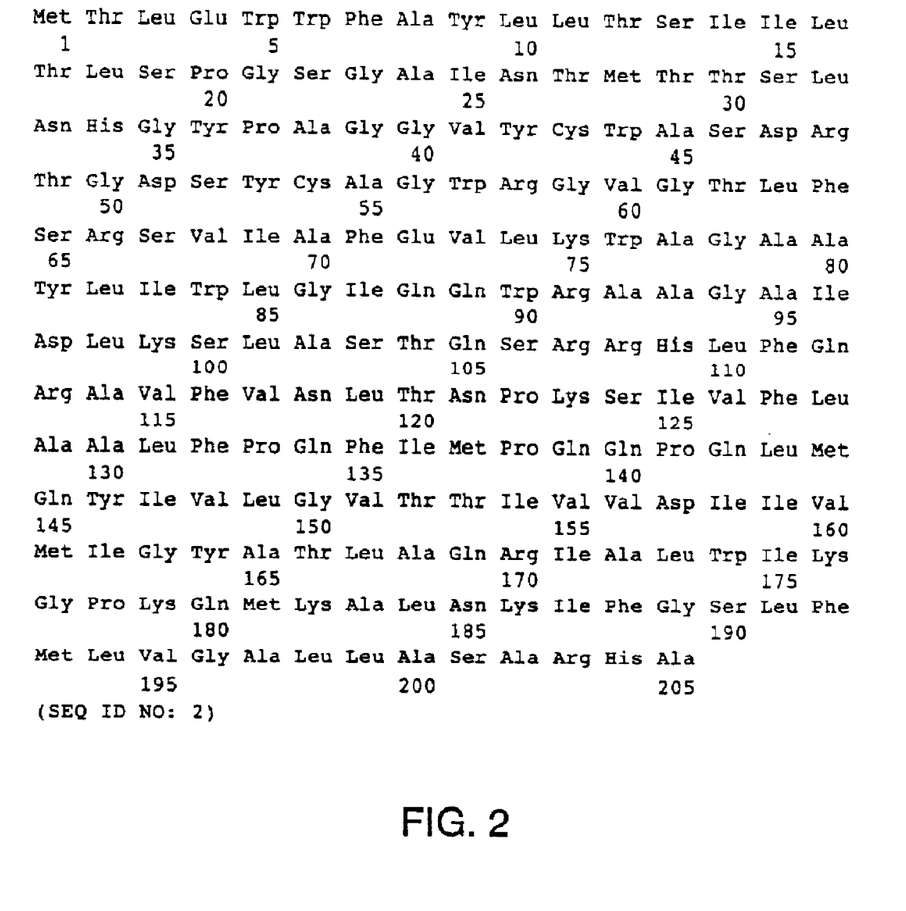
FIG. 2 shows the amino acid sequence of the RhtB protein SEQ ID NO:2).

The wild-type rhtB gene was cloned in vivo using mini-Mu d5005 phagemid (Groisman, E. A., et al., J. Bacteriol., 168, 357–364 (1986)). MuCts62 lysogen of the strain MG442 was used as a donor. Freshly prepared lysates were used to infect a Mucts lysogenic derivative of a strain VKPM B-513 (Hfr K10 metB). The cells were plated on M9 glucose minimal medium with methionine (50 µg/ml), kanamycin (40 µg/ml) and homoserine (10 mg/ml). Colonies which appeared after 48 hr were picked and isolated. Plasmid DNA was isolated and used to transform the strain VKPM B-513 by standard techniques. Transformants were selected on L-broth agar plates with kanamycin as above. Plasmid DNA was isolated from those which were resistant to homoserine, and analyzed by restriction mapping of the structure of the inserted fragments. It appeared that two types of inserts belonging to different chromosome regions had been cloned from the donor. Thus, at least two different genes that is in multicopy and imparts resistance to homoserine exist in *E. coli*. One of the two type of inserts is the rhtA gene which has already reported (ABSTRACTS of 17th International Congress of Biochemistry and Molecular Biology in conjugation with 1997 Annual Meeting of the American Society for Biochemistry and Molecular Biology, San Francisco, Calif. Aug. 24–29, 1997). Among the other of the two types of inserts, a fragment of a minimum length which imparts the resistance to homoserine is of 0.8 kb (FIG. 1).

(2) Identification of rhtB Gene

The insert fragment was sequenced by the dideoxy chain termination method of Sanger. Both DNA strands were sequenced in their entirety and all junctions were overlapped. The sequencing showed that the insert fragment included f138 (nucleotide numbers 61543 to 61959 of GenBank accession number M87049) which was a known but function-unknown ORF (open reading frame) present at 86 min of *E. coli* chromosome and 201 bp of an upstream region thereof (downstream region in the sequence of M87049). The f138 which had only 160 nucleotides in the 5'-flanking region could not impart the resistance to homoserine. No termination codon is present upstream the ORF f138 between 62160 and 61959 nucleotides of M87049. Furthermore, one ATG following a sequence predicted as a ribosome binding site is present in the sequence. The larger ORF (nucleotide numbers 62160 to 61546) is designated as rhtB gene. The RhtB protein deduced from the gene is highly hydrophobic and contains 5 possible transmembrane segments.

Example 2

Production of Homoserine-producing Strain

Strain NZ10 of *E. coli* was transformed by a plasmid pAL4 which was a pBR322 vector into which the thrA gene coding for aspartokinase-homoserine dehydrogenase I was inserted, to obtain the strains NZ10/pAL4. The strain NZ10 is a leuB$^+$-reverted mutant (thrB) obtained from the *E. coli* strain C600 (thrB, leuB) (Appleyard, Genetics, 39, 440–452 (1954)).

The rhtB gene was inserted to a plasmid pUK21 which is a known plasmid pUC19 in which a kanamycin resistance gene substituted for an ampicillin resistance gene (Vieira, J. and Messing, J., Gene, 100, 189–194 (1991)), to obtain pRhtB.

The strain NZ10/pAL4 was transformed with pUK21 or pRhtB to obtain strains NZ10/pAL4,pUK21 and NZ10/pAL4,pRhtB.

The thus obtained transformants were each cultivated at 37° C. for 18 hours in a nutrient broth with 50 mg/l kanamycin and 100 mg/l ampicillin, and 0.3 ml of the obtained culture was inoculated into 3 ml of a fermentation medium having the following composition and containing 50 mg/l kanamycin and 100 mg/l ampicillin, in a 20×200 mm test tube, and cultivated at 37° C. for 46 hours with a rotary shaker. After the cultivation, an accumulated amount of homoserine in the medium and an absorbance at 560 nm of the medium were determined by known methods.

| Fermentation medium composition | (g/L) |
| --- | --- |
| Glucose | 80 |
| $(NH_4)_2SO_4$ | 22 |
| $K_2HPO_4$ | 2 |
| NaCl | 0.8 |

-continued

| Fermentation medium composition | (g/L) |
|---|---|
| MgSO$_4$.7H$_2$O | 0.8 |
| FeSO$_4$.7H$_2$O | 0.02 |
| MnSO$_4$.5H$_2$O | 0.02 |
| Thiamine hydrochloride | 0.0002 |
| Yeast Extract | 1.0 |
| CaCO$_3$ | 30 |

(CaCO$_3$ was separately sterilized.)

The results are shown in Table 1. As shown in Table 1, the strain NZ10/pAL4,pRhtB accumulated homoserine in a larger amount than the strains NZ10/pAL4 and NZ10/pAL4, pUK21 in which the rhtB gene was not enhanced.

TABLE 1

| Strain | OD$_{560}$ | Accumulated amount of homoserine (g/L) |
|---|---|---|
| NZ10/pAL4 | 16.4 | 3.1 |
| NZ10/pAL4,pUK21 | 14.3 | 3.3 |
| NZ10/pAL4,pRhtB | 15.6 | 6.4 |

Example 3

Production of Alanine, Valine and Isoleucine with pRhtB-introduced Strain

E. coli strain MG442 is a known strain (Gusyatiner, et al., 1978, Genetika (in Russian), 14:947–956).

The strain MG442 was transformed with the plasmids pUK21 and pRhtB to obtain strains MG442/pUK21 and MG442/pRhtB.

The thus obtained transformants were each cultivated at 37° C. for 18 hours in a nutrient broth with 50 mg/l kanamycin, and 0.3 ml of the obtained culture was inoculated into 3 ml of the fermentation medium described in Example 2 and containing 50 mg/l kanamycin, in a 20×200 mm test tube, and cultivated at 37° C. for 40 hours with a rotary shaker. After the cultivation, accumulated amounts of alanine, valine and isoleucine in the medium and an absorbance at 560 nm of the medium were determined by known methods.

The results are shown in Table 2. As shown in Table 2, the strain MG442/pRhtB accumulated each of alanine, valine and isoleucine in a larger amount than the strain MG442/pUK21 in which the rhtB gene was not enhanced.

TABLE 2

| | | Accumulated amount (g/L) | | |
|---|---|---|---|---|
| Strain | OD$_{560}$ | Alanine | Valine | Isoleucine |
| MG442/pUK21 | 13.4 | 0.2 | 0.2 | 0.3 |
| MG442/pRhtB | 13.7 | 0.7 | 0.5 | 0.5 |

Example 4

Production of Threonine-producing Strain

The strain MG442 (Example 3) was transformed by introducing a known plasmid pVIC40 (U.S. Pat. No. 5,175, 107 (1992)) by an ordinary transformation method. Transformants were selected on LB agar plates containing 0.1 mg/ml streptomycin. Thus a novel strain MG422/pVIC40 was obtained.

The strain MG442/pVIC40 was transformed with pUK21 or pRhtB to obtain strains MG442/pVIC40,pUK21 and MG442/pVIC40,pRhtB.

The thus obtained transformants were each cultivated at 37° C. for 18 hours in a nutrient broth with 50 mg/l kanamycin and 100 mg/l streptomycin, and 0.3 ml of the obtained culture was inoculated into 3 ml of the fermentation medium described in Example 2 and containing 50mg/l kanamycin and 100 mg/l streptomycin, in a 20×200 mm test tube, and cultivated at 37° C. for 46 hours with a rotary shaker. After the cultivation, an accumulated amount of threonine in the medium and an absorbance at 560 nm of the medium were determined by known methods.

The results are shown in Table 3. As shown in Table 3, the strain MG442/pVIC40,pRhtB accumulated threonine in a larger amount than the strains MG442/pVIC40 and MG442/pVIC40,pUK21 in which the rhtB gene was not enhanced.

TABLE 3

| Strain | OD$_{560}$ | Accumulated amount of threonine (g/L) |
|---|---|---|
| MG442/pVIC40 | 17 | 13.6 |
| MG442/pVIC40,pUK21 | 16.3 | 12.9 |
| MG442/pVIC40,pRhtB | 15.2 | 16.3 |

Example 5

Effect of rhtB Gene Inactivation and Amplification on Bacterium E. coli Resistance to Some Amino Acids and Amino Acid Analogues To inactivate the chromosomal rhtB gene the plasmid pNPZ46 was constructed (FIG. 1) on the basis of pUK21 vector. It harbors a DNA fragment from 86 min of E. coli chromosome, with the rhtB gene and 5'-flanking and 3'-flanking regions thereof. Then the ClaI-Eco47III fragment of the pNPZ46 plasmid rhtB gene was substituted for AsuII-BsrBI fragment containing cat (Cm$^R$) gene of pACYC184 plasmid (Chang and Cohen, J. Bacteriol., 134, 1141–1156, 1978) giving the pNPZ47 plasmid (FIG. 1). To introduce the obtained insertionally inactivated rhtB gene into the chromosome of the E. coli strain N99 (the streptomycin-resistant derivative of the known strain W3350 (Campbell, Virology, 14, 22–33, 1961)), the method of Parker and Marinus was used (Parker, B. and Marinus, M. G., Gene, 73, 531–535, 1988). The substitution of the wild type allele for the inactivated one was proved by phage P1 transduction and by Southern hybridization (Southern, E. M., J. Mol. Biol., 98, 503–517, 1975).

Then the susceptibility of the thus obtained E. coli strain N99 rhtB::cat, of the initial strain N99 (rhtB$^+$) and of its derivative transformed with pRhtB plasmid, N99/pRhtB, to some amino acids and amino acid analogues was tested. overnight cultures of the strains grown in M9 minimal medium at 37° C. with a rotary shaker (10$^9$ cfu/ml) were diluted 1:100 and grown for 5 hours under the same conditions. Then the log phase cultures thus obtained were diluted and about 10$^4$ of alive cells were applied to welldried test plates with M9 agar containing doubling increments of amino acids or analogues. The minimum inhibitory concentration (MIC) of these compounds were examined after 40–46 h cultivation. The results are shown in Table 4.

TABLE 4

|  | MIC (µg/ml) | | |
| --- | --- | --- | --- |
| Substrate | N99 (rhtB+) | N99/pRhtB | N99 rhtB::cat |
| 1. L-homoserine | 250 | 30000 | 125 |
| 2. L-threonine | 30000 | 50000 | 30000 |
| 3. L-serine | 5000 | 10000 | 5000 |
| 4. L-valine | 0.5 | 1 | 0.5 |

TABLE 4-continued

|  | MIC (µg/ml) | | |
| --- | --- | --- | --- |
| Substrate | N99 (rhtB+) | N99/pRhtB | N99 rhtB::cat |
| 5. AHVA | 50 | 2000 | 25 |
| 6. AEC | 10 | 25 | 10 |
| 7. 4-aza-DL-leucine | 40 | 100 | 40 |

It follows from the Table 4 that multiple copies of rhtB besides homoserine confered upon cells increased resistance to threonine, serine, valine, α-amino-α-hydroxyvaleric-acid (AHVA), S-(2-aminoethyl)-L-cysteine (AEC), and 4-aza-DL-leucine. The inactivation of the rhtB gene, on the contrary, increased the cell sensitivity to homoserine and AHVA. These results in conjunction with the data on homology of the RhtB protein to LysE lysine efflux transporter of *Corynebacterium glutamicum* (Vrljic et al., Mol. Microbiol., 22, 815–826, 1996) indicate the analogues function for the rhtB gene product. The presumed efflux transporters, RhtB, has specificity to several substrates (amino acids), or may show non-specific effects as a result of amplification.

What is claimed is:

1. A method for producing an amino acid selected from the group consisting of L-threonine, L-homoserine, L-alanine, L-isoleucine and L-valine, comprising:

cultivating a bacterium which has an ability to produce and cause accumulation of the amino acid in a culture medium, and recovering the amino acid from the medium, wherein said bacterium is a bacterium belonging to the genus *Escherichia*, wherein L-homoserine resistance of said bacterium is enhanced by amplifying a copy number of a DNA in said bacterium, wherein said DNA codes for a protein comprising the amino acid sequence shown in SEQ ID NO:2.

2. The method according to claim 1, wherein said amino acid is at least one selected from the group consisting of L-alanine, L-isoleucine, and L-valine.

3. The method according to claim 1, wherein said DNA is carried on a multicopy vector.

4. The method according to claim 1, wherein said DNA is carried on a transposon.

5. The method according to claim 1, wherein said DNA comprises nucleotides 557 to 1171 of SEQ ID NO:1.

* * * * *

SEQUENCE LISTING

<160> NUMBER OF SEQ ID NOS: 2

<210> SEQ ID NO 1
<211> LENGTH: 1200
<212> TYPE: DNA
<213> ORGANISM: Escherichia coli
<220> FEATURE:
<221> NAME/KEY: CDS
<222> LOCATION: (557)..(1171)

<400> SEQUENCE: 1

```
agaaataatg tggagatcgc accgcccatc gaatgtgcca gtatatagcg tttacgccac      60
ggaccgggct gaacctcctg ctgccagaat gccgccagat catcaacata atcattaaag     120
cgattaacat gcccgagatg cggatcggct aacaggcgac cggaacgtcc ctgcccgcga     180
tggtcgatga ttaagacatc aaaccccaaa tggaacaggt cataggccag ttccgcatat     240
tttacgtagc tctcaatacg ccccgggcag atgactacca cccggtcatg gtgctgtgcg     300
cgaaaacgga caaagcgcac cggaatgtca tccacaccag taaactctgc ttcatcacgc     360
tgacgccaga aatcagtcag cggtcccatg gtaaaagcag caaacgcgtt ttctcttgtt     420
tcccagtctt tttgctgctg aaacatcggg taatctgcct cttaaaccac gtaaaatcgt     480
tttttttagc gtgcctgaca caacgctgcg acagtagcgt attgtggcac aaaaatagac     540
acaccgggag ttcatc atg acc tta gaa tgg tgg ttt gcc tac ctg ctg aca    592
              Met Thr Leu Glu Trp Trp Phe Ala Tyr Leu Leu Thr
                1               5                   10 tcg atc att tta acg ctg tcg cca ggc tct ggt gca atc aac act atg    640
Ser Ile Ile Leu Thr Leu Ser Pro Gly Ser Gly Ala Ile Asn Thr Met
            15                  20                  25 acc acc tcg ctc aac cac ggt tat ccg gcc ggt ggc gtc tat tgc tgg    688
Thr Thr Ser Leu Asn His Gly Tyr Pro Ala Gly Gly Val Tyr Cys Trp
        30                  35                  40 gct tca gac cgg act ggc gat tca tat tgt gct ggt tgg cgt ggg gtt    736
Ala Ser Asp Arg Thr Gly Asp Ser Tyr Cys Ala Gly Trp Arg Gly Val
45                  50                  55                  60 ggg acg cta ttt tcc cgc tca gtg att gcg ttt gaa gtg ttg aag tgg    784
```

-continued

```
                                                                             832
Gly Thr Leu Phe Ser Arg Ser Val Ile Ala Phe Glu Val Leu Lys Trp
                 65                  70                  75
gca ggc gcg gct tac ttg att tgg ctg gga atc cag cag tgg cgc gcc        832
Ala Gly Ala Ala Tyr Leu Ile Trp Leu Gly Ile Gln Gln Trp Arg Ala
                 80                  85                  90 gct ggt gca att gac ctt aaa tcg ctg gcc tct act caa tcg cgt cga        880
Ala Gly Ala Ile Asp Leu Lys Ser Leu Ala Ser Thr Gln Ser Arg Arg
             95                 100                 105 cat ttg ttc cag cgc gca gtt ttt gtg aat ctc acc aat ccc aaa agt        928
His Leu Phe Gln Arg Ala Val Phe Val Asn Leu Thr Asn Pro Lys Ser
         110                 115                 120 att gtg ttt ctg gcg gcg cta ttt ccg caa ttc atc atg ccg caa cag        976
Ile Val Phe Leu Ala Ala Leu Phe Pro Gln Phe Ile Met Pro Gln Gln
125                 130                 135                 140 ccg caa ctg atg cag tat atc gtg ctc ggc gtc acc act att gtg gtc       1024
Pro Gln Leu Met Gln Tyr Ile Val Leu Gly Val Thr Thr Ile Val Val
                145                 150                 155 gat att att gtg atg atc ggt tac gcc acc ctt gct caa cgg att gct       1072
Asp Ile Ile Val Met Ile Gly Tyr Ala Thr Leu Ala Gln Arg Ile Ala
                160                 165                 170 cta tgg att aaa gga cca aag cag atg aag gcg ctg aat aag att ttc       1120
Leu Trp Ile Lys Gly Pro Lys Gln Met Lys Ala Leu Asn Lys Ile Phe
                175                 180                 185 ggc tcg ttg ttt atg ctg gtg gga gcg ctg tta gca tcg gcg agg cat       1168
Gly Ser Leu Phe Met Leu Val Gly Ala Leu Leu Ala Ser Ala Arg His
        190                 195                 200 gcg tgaaaaataa tgtcggatgc ggcgtaaac                                    1200
Ala
205

<210> SEQ ID NO 2
<211> LENGTH: 205
<212> TYPE: PRT
<213> ORGANISM: Escherichia coli

<400> SEQUENCE: 2

Met Thr Leu Glu Trp Trp Phe Ala Tyr Leu Leu Thr Ser Ile Ile Leu
 1               5                  10                  15

Thr Leu Ser Pro Gly Ser Gly Ala Ile Asn Thr Met Thr Thr Ser Leu
                20                  25                  30

Asn His Gly Tyr Pro Ala Gly Val Tyr Cys Trp Ala Ser Asp Arg
             35                  40                  45

Thr Gly Asp Ser Tyr Cys Ala Gly Trp Arg Gly Val Gly Thr Leu Phe
         50                  55                  60

Ser Arg Ser Val Ile Ala Phe Glu Val Leu Lys Trp Ala Gly Ala Ala
65                  70                  75                  80

Tyr Leu Ile Trp Leu Gly Ile Gln Gln Trp Arg Ala Ala Gly Ala Ile
                 85                  90                  95

Asp Leu Lys Ser Leu Ala Ser Thr Gln Ser Arg Arg His Leu Phe Gln
            100                 105                 110

Arg Ala Val Phe Val Asn Leu Thr Asn Pro Lys Ser Ile Val Phe Leu
        115                 120                 125

Ala Ala Leu Phe Pro Gln Phe Ile Met Pro Gln Gln Pro Gln Leu Met
    130                 135                 140

Gln Tyr Ile Val Leu Gly Val Thr Thr Ile Val Val Asp Ile Ile Val
145                 150                 155                 160

Met Ile Gly Tyr Ala Thr Leu Ala Gln Arg Ile Ala Leu Trp Ile Lys
                165                 170                 175
```

```
-continued

Gly Pro Lys Gln Met Lys Ala Leu Asn Lys Ile Phe Gly Ser Leu Phe
            180                 185                 190

Met Leu Val Gly Ala Leu Leu Ala Ser Ala Arg His Ala
            195                 200             205
```